(12) United States Patent
Kern

(10) Patent No.: US 11,278,699 B2
(45) Date of Patent: Mar. 22, 2022

(54) INHALATION METHOD WITH CONTROLLED CYCLIC ACTIVATION

(71) Applicant: NEBU-TEC MED. PRODUKTE EIKE KERN GMBH, Elsenfeld (DE)

(72) Inventor: Stefan Kern, Elsenfeld (DE)

(73) Assignee: NEBU-TEC MED. PRODUKTE EIKE KERN GMBH, Elsenfeld (DE)

( * ) Notice: Subject to any disclaimer, the term of this patent is extended or adjusted under 35 U.S.C. 154(b) by 636 days.

(21) Appl. No.: 16/317,136

(22) PCT Filed: Jul. 13, 2017

(86) PCT No.: PCT/DE2017/100581
§ 371 (c)(1),
(2) Date: May 17, 2019

(87) PCT Pub. No.: WO2018/010733
PCT Pub. Date: Jan. 18, 2018

(65) Prior Publication Data
US 2019/0290879 A1    Sep. 26, 2019

(30) Foreign Application Priority Data
Jul. 14, 2016   (DE) .................... 10 2016 112 986.0

(51) Int. Cl.
*A61M 16/14* (2006.01)
*A61M 15/00* (2006.01)
(Continued)

(52) U.S. Cl.
CPC ............ *A61M 16/14* (2013.01); *A61M 11/00* (2013.01); *A61M 11/005* (2013.01);
(Continued)

(58) Field of Classification Search
CPC ............ A61M 16/14; A61M 15/0086; A61M 15/0085; A61M 15/0021; A61M 11/005; A61M 15/00
See application file for complete search history.

(56) References Cited

U.S. PATENT DOCUMENTS

2004/0112380 A1*   6/2004   Djupesland ............ A61B 5/415
                                                    128/203.12
2005/0217666 A1*   10/2005  Fink ................... A61K 31/7036
                                                    128/200.14
(Continued)

FOREIGN PATENT DOCUMENTS

| DE | 19720701 A1 | 11/1998 |
|---|---|---|
| DE | 102006026786 A1 | 12/2007 |
| WO | 2018010733 A1 | 1/2018 |

OTHER PUBLICATIONS

International Search Report and Written Opinion of PCT/DE2017/100581, dated Dec. 15, 2017.

*Primary Examiner* — Margaret M Luarca
(74) *Attorney, Agent, or Firm* — Westman, Champlin & Koehler, P.A.

(57) ABSTRACT

In a method for performing an inhalation a reservoir is filed with a medication fluid or a medication container is connected to a designated connecting piece, a nebulizer unit is connected to a control unit and a mouthpiece, the nebulizer unit is activated, the medication fluid is atomized into a fine particulate aerosol which is emitted into an aerosol chamber formed by the nebulizer unit and the mouthpiece, and an inhalation is performed by a user. A pressure within the aerosol chamber and/or a flow rate through the aerosol chamber is measured using the control unit. The nebulizer is activated with each breath on occurrence of at least one (Continued)

activation criterion detected using the control unit. The nebulizer unit is deactivated with fulfillment of at least one stop criterion.

24 Claims, 2 Drawing Sheets

(51) Int. Cl.
*A61M 16/00* (2006.01)
*A61M 11/00* (2006.01)

(52) U.S. Cl.
CPC .... *A61M 15/0021* (2014.02); *A61M 15/0085* (2013.01); *A61M 15/0086* (2013.01); *A61M 16/0069* (2014.02); *A61M 16/024* (2017.08); *A61M 2016/0018* (2013.01); *A61M 2016/0027* (2013.01); *A61M 2016/0039* (2013.01); *A61M 2205/3365* (2013.01)

(56) References Cited

U.S. PATENT DOCUMENTS

2009/0025718 A1* 1/2009 Denyer ................ A61M 11/005
128/203.14
2010/0282247 A1 11/2010 Kadrichu et al.
2012/0037154 A1* 2/2012 Gallem ............. A61M 15/0015
128/200.16
2016/0175545 A1 6/2016 Fink et al.

* cited by examiner

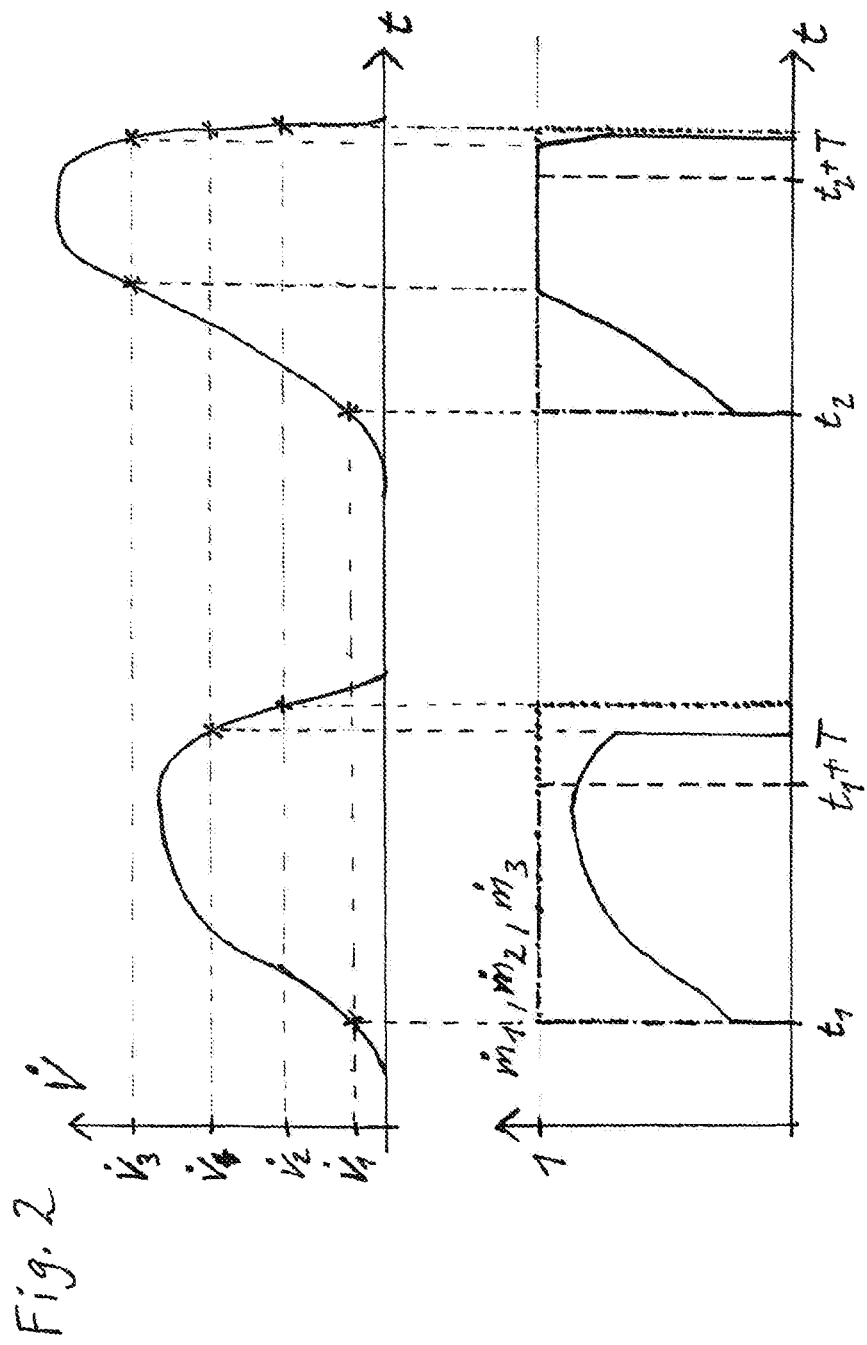

INHALATION METHOD WITH CONTROLLED CYCLIC ACTIVATION

CROSS-REFERENCE TO RELATED APPLICATION

This application is a Section 371 National Stage Application of International Application No. PCT/DE2017/100581, filed Jul. 13, 2017, the content of which is incorporated herein by reference in its entirety, and published as WO 2018/010733 on Jan. 18, 2018, not in English.

FIELD

Embodiments of the present disclosure relate to methods for performing inhalation using a nebulizer, and a nebulizer suitable for performing the method.

BACKGROUND

In the case of diseases of the respiratory tract, in particular of the larynx, bronchial tubes, alveolae or else the air sacs themselves, an inhalation therapy is often the most efficient and, most importantly, the most effective method for administering a medication to the desired place of action. For performing such inhalation therapy, so-called nebulizers are used today, in which a medication formulation, which is present in liquid form, is atomized by means of an atomizing unit to form a fine-particulate aerosol. The droplet size to be reached, here, depends on at which point in the respiratory tract the medication ought to be deposited. In the case of diseases of the bronchial tubes, larger droplet diameters are permissible or necessary compared to diseases of the air sacs, which can only be reached by the droplets of the aerosol if the droplet radius lies within the range of a few micrometers.

The atomization unit used in modern nebulizers usually consists of a so-called mesh-membrane, that is to say a fine metal membrane with microscopically small, funnel-shaped holes in a central region of the membrane, which usually has a circular outline, and a vibration generator that is mechanically coupled to the membrane and sets it into rapid vibrations typically lying in the ultrasonic range. The medication fluid is usually enclosed in a medication reservoir that is integrated in the nebulizer unit and is in direct contact with the atomization unit or the mesh membrane, so that on oscillation of the membrane, medication liquid is forced through the funnel-shaped perforations of the membrane and an aerosol in the form of a fine-particulate mist is generated at the outlet end of the membrane.

In the nebulizers that are usually used today, there is the disadvantage that the atomization of the medication fluid takes place continuously via the entire duration of the inhalation process, that is to say both while the patient inhales and exhales. During the exhalation process, however, no medication can naturally pass into the lungs, as a result of which the medication atomized at this time precipitates in the mouthpiece at the outlet end of the atomization unit and is thus lost unused. A collection and reuse of this deposit is precluded because of hygienic concerns, since the space at the outlet end of the aerosol generator is non-sterile.

To avoid these losses, it would thus be desirable if the atomization process only took place during the inhalation process. Such a controlled atomization is known from the prior art for artificial respirators, which are used as stationary, relatively complex and expensive devices in hospitals for ventilation of patients in intensive care units. In such machines, a detailed monitoring of the respiration cycle, including monitoring of the pressure and/or flow, takes place, resulting in a corresponding control of a nebulizer that is connected for control purposes to such an artificial respirator.

In the case of mobile, that is to say portable, nebulizers, a triggering or other control is not known in general. That is to say, such devices continually atomize the medication fluid during an inhalation with the above-described disadvantageous consequences. This is because the sensor device associated with a monitoring of the respiration course would make the device very complex and therefore also expensive.

One possibility of performing a controlled activation of the atomization process, which is also suitable for portable units because of its relatively simple implementation is described in the patent document EP 1 304 131 B1. Here, it is taught that an output signal of the atomization device itself, that is to say of the vibration generator, which is mechanically coupled to the mesh membrane and comprises an electromechanical piezocrystal, can be used to start the atomization process. The disadvantage of this is that this output signal of the pressure change which acts on the membrane varies as a result of the starting respiration process, and thus also responds sensitively to shocks of the inhaler. This is particularly disadvantageous in the case of portable, hand-held inhalers, since these shocks take place irregularly and unpredictably. The progress of the breathing operation can therefore only take place approximately with the aid of this output signal.

SUMMARY

Embodiments of the present disclosure relate to a method for performing inhalation using a nebulizer and a nebulizer for performing the method. In one embodiment of the method, a reservoir is filled with a medication fluid into a reservoir or connecting a medication container to a designated connecting piece, possibly connecting a nebulizer unit to a control unit and/or mounting a mouthpiece, at least temporarily activating the nebulizer unit, during the activation, the medication fluid being atomized into a fine particulate aerosol which is emitted into an aerosol chamber which is formed by the nebulizer unit and mouthpiece, performing the inhalation, the user enclosing the mouthpiece with the lips and during inhalation, drawing air from outside into the aerosol chamber, where the air mixes with the aerosol, and then passes further through the mouthpiece into the respiratory tract and, possibly into the lung of the user. The invention further describes a nebulizer suitable for performing the method.

One object of the present invention is therefore to find a process for performing an inhalation and to develop a nebulizer, which is suitable for performing this method and permits a most efficient and effective use of medication, even when the nebulizer has a portable design.

In some embodiments, this object is achieved by a method for inhalation and a nebulizer for performing this method according to the independent claims.

One embodiment of the nebulizer is designed such that, on the nebulizer unit, which contains the mesh membrane with the piezo vibration generator coupled thereto has, as aerosol generator, an air channel, which, at one end, opens into the interior of the nebulizer unit in the aerosol unit, which is disposed in the outlet end of the aerosol generator, and at its second end, is led out of the nebulizer unit and can be connected to the control unit. By this means, it is achieved that, in the control unit, a suitable sensor for measuring a pressure and/or a flow through the mouthpiece can be installed, which is in fluid communication with the interior of the nebulizer unit.

The advantage of a nebulizer designed in this way is that the first end of the nebulizer can open at a most suitable point in the interior of the nebulizer unit at the outlet end of the aerosol generator, at which a pressure difference during the course of the respiratory process is maximum. The sensor, which is specifically used in the control unit, for monitoring the pressure and/or flow through the mouthpiece can then be selected within a certain scope. An optimization regarding different criteria can take place. On one hand, a most technically simple solution could be realized, in which a simple pressure sensor is used, which responds to a change of the total pressure. This consists of a sum of the static and dynamic pressure. In the course of a breath, the former is first depressed, whereupon, due to the aerosol chamber and the mouthpiece, an air stream transporting away the aerosol forms, which is reflected in a reduced dynamic pressure. If only one or other component is to be measured, a design similar to a Pitot's tube, used for velocity measurement in aircraft, could be implemented, which permits an automatic differential pressure formation. For the purposes of aerosol production control, however, a measurement of the total pressure is sufficient in practice.

If a direct stream or flow measurement is desired, a heated resistor can be used and the temperature change due to the air stream through the flow channel can be measured, or a miniaturized impeller can be used, which is operated by the air stream and the speed of which is proportional to the flow rate.

Since the accuracy of measurement of such a dedicated external sensor is higher than that of one seated within the nebulizer unit, in particular if the output signal of the aerosol generator itself is interpreted as a sensor signal and indicator of the suction pressure, it is possible to achieve a control of the aerosol production that is better adapted to the respiratory profile.

The method according to some embodiments of the present disclosure for performing an inhalation now provides that a nebulizer, which has a pressure and/or flow-rate sensor, is actuated such that the atomization/aerosol production is started as soon as a start criterion is met, and is stopped when a stop criterion is reached.

The possible start criteria can be chosen depending on the sensitivity and possibilities of the sensor, and include: activation on exceeding the threshold of the flow rate (air volume per unit time), activation on falling below a threshold pressure, activation on reaching a particular total flow rate (volume) or activation on exceeding a threshold value for a target attainment probability, which is dynamically calculated by the control unit using the respiratory profile previously measured. In the simplest case, the activation takes place in the form of a triggering, in which the inhalation is switched from completely off (0% aerosol production) to completely on (100% of maximum aerosol production rate). Instead of a simple triggering, slow or continuous increase of the emitted aerosol amount can be provided, for example according to the formula:

$$\frac{\dot{m}}{\dot{m}_{max}} = \mathrm{Min}\left[1, \mathrm{Max}\left[0, \frac{X - X_1}{X_1 - X_2}\right]\right]$$

Here, $\dot{m}$ denotes the current and $\dot{m}_{max}$, the maximum aerosol production rate (mass per time) and X or $X_1$, $X_2$, the current value or threshold values of the control parameter (pressure, flow rate, flow quantity or target attainment probability) that is used in each case.

The stop criteria, at which the aerosol generation, that is to say the atomization, is terminated, may comprise: expiry of a predetermined time span, falling below a second threshold value for the flow rate and/or exceeding a second threshold value for the pressure and/or reaching a second threshold value for the total flow rate and/or exceeding a second threshold value for the probability that an aerosol particle emitted at that moment reaches its target in the respiratory tracts of the user.

The threshold values for activation and deactivation could also be selected to be identical, however, in practice, this is not usually useful, since one usually wants to perform the activation as early as possible with each breath and therefore chooses threshold values that are as close as possible to the equilibrium value (without respiration). On the other hand, the switching off/deactivation of production should if possible take place when the air passing through the aerosol chamber at that moment would probably no longer pass into the target area, which, in view of the finite dead volume in the mouthpiece, mouth cavity and, possibly, a tube connecting nebulizer unit and mouthpiece, is usually the case significantly before the threshold value used for activation is reached (again).

Concerning the type of disconnection, it is usually conceivable that, besides a simple, immediate switching off (stop triggering), a continuous reduction of the aerosol production to zero takes place, for example, as with the activation above, the aerosol production rate is chosen proportional to the standardized difference of a control parameter and a threshold value. However, other, non-proportional, profiles can be provided.

The advantages of the method according to some embodiments of the present disclosure are diverse. On one hand, in a simple embodiment, a straightforward triggering can take place, which functions very simply and reliably, specifically with the aid of a registered pressure or flow value. The essential advantage is that aerosol production does not take place if an aerosol particle probably does not reach its target, that is to say in particular during the exhalation process. By this means, the method according to some embodiments of the present disclosure for performing the inhalation ensures that, in a simple manner and with simple means, since it only requires a single sensor, ensures that aerosol production only takes place when it is required, that is to say when the medication can be effective.

The advantageous consequences of this are first that, at the outlet end of the aerosol generator in the nebulizer unit, as well as in the mouthpiece, no condensate from medication fluid that has not been exhaled and is deposited on the walls, forms, which reduces the need for cleaning and is more hygienic overall. On the other hand, the density of the aerosol mist is reduced at the beginning of the inhalation process, which reduces the tendency for the user to suffer an irritation of the throat, which might interrupt the inhalation for some time and, due to premature removal of the medication, also reduce the effect of the inhalation or compromise it altogether. A tendency to irritation of the throat can advantageously be further reduced if, when the activation, that is to say the start criterion is reached, no simple triggering of aerosol production takes place, but the production, as described above, is continuously increased to the maximum value.

Since aerosol production only takes place when it is required, expensive medication is advantageously saved, and thereby the costs of a therapy advantageously significantly reduced. The beginning of aerosol production, and its termination, that is to say the deactivation is possible either before execution of the inhalation or else dynamically during the inhalation due to the measured actual pressure or flow conditions. Herein, the start as well as the stop criteria that are used can be adapted, that is to say the threshold values for pressure and/or flow rate, or the total flow rate determined to that point or the target attainment probability are increased or reduced. If necessary, the rate can also be changed, in which the aerosol generation after a triggering is increased and/or reduced to the maximum value. With a simple immediate termination of aerosol production after expiry of a time span, the aerosol production can also be determined in advance or dynamically adapted. The control takes place in all cases via the control unit of the nebulizer according to some embodiments of the present disclosure, in which either the user manually sets his desired parameters or the control unit allows an automatic, dynamic adjustment to be performed.

A further advantage, which cannot be neglected in the case of portable nebulizers consists in the fact that, due to the more efficient, only temporary activation of aerosol production, the battery of the device is preserved.

Further advantageous embodiments of the present disclosure, which can be realized individually or in combination, in so far as they do not obviously preclude one another are described below.

Some embodiments of the present disclosure propose that, in the course of monitoring the respiration profile from the control unit, an integration of the measured flow rate takes place, so that the inhaled air quantity, that is to say the respiratory volume, is also known. This can then also be used for activation as well as for deactivation of aerosol production, wherein, for example, an activation takes place when a certain first threshold value is exceeded and the deactivation takes place when a certain second threshold value is exceeded.

Alternatively, in the control unit, an approximate target attainment probability can be computed, which indicates how probable it is that an aerosol particle produced at a certain time arrives at its target location in the respiratory tracts of the user. This probability takes in to account, on one hand, the target location to be reached, that is to say whether the aerosol in the bronchial tubes, the alveolae or air sacs is to be deposited and on the other hand on the residual respiratory volume still remaining. Herein, it is advantageous if the entire volume of a breath is known. This can either be measured in advance by other means and the measured value be stored in the control unit, or it is determined by the nebulizer according to some embodiments of the present disclosure during the inhalation itself and, in certain circumstances, also dynamically adapted to a changing respiratory behaviour of the user.

As criterion for starting aerosol production, the following come into consideration: exceeding a threshold value of the flow, falling below a threshold value of the pressure, exceeding a total flow rate, exceeding a threshold value for the target attainment probability. As stop criteria, the following come into consideration: expiry of a time span since the activation of aerosol production, falling below a second threshold value of the flow rate, exceeding a second threshold value of the pressure, exceeding a second threshold value of the total flow rate, and/or falling below a second threshold value of the target attainment probability. Herein, the used first and second threshold values can also be identical. It should be emphasised that some embodiments of the present disclosure provide that the start and stop criteria can be arbitrarily combined with one another, that is to say it for starting, that is to say for activating aerosol production, for example the exceeding of a threshold value of the flow rate for completing aerosol production, but the reaching of a certain threshold value of the total flow rate can be used.

All threshold values can be preset and unchangeable, or chosen by the user himself before inhalation. In addition, it is conceivable that the control unit performs a dynamic adaptation to actually measured values. If, for example, it is ascertained that a total flow rate, that is to say respiratory volume always lies below a threshold value, this can be reduced. If, on the other hand, the respiratory volume lies significantly above the threshold value, this can be increased to utilize a larger proportion of the inhalation phase.

Threshold values can also be used in combination, that is to say the control unit simultaneously monitors multiple criteria and starts or stops aerosol production because of the occurrence of all or at least one criterion. This is in particular appropriate when a total flow rate/respiratory volume is used as stop criterion. To avoid the non-reaching of the deactivation threshold value, e.g. the continuation of aerosol production due to shallow breathing or a small lung volume, the disconnection may additionally take place after expiry of a time span.

As generalization, some embodiments of the present disclosure propose that the control unit determines a degree of fulfillment, that is to say a percentage value, for each criterion, which, depending on the nature of the control parameter and the process (activation/deactivation), in the simplest case These degrees of fulfillment can then be calculated by the control unit with weighting factors on the part of the user or else fixed predetermined or else adaptable in the course of inhalation to form a weighted average degree of fulfillment. Activation or deactivation of aerosol production then takes place in such a method when the degree of fulfillment of the first and second threshold values are reached.

The pressure measurement then preferably takes place by means of a pressure sensor in the control unit, which, due to the flow channel of the nebulizer being in fluid communication with the outlet end of the aerosol generator, so that the pressure changes there can be registered by the sensor within the control unit. Alternatively, a direct flow measurement may also take place, either in that the back pressure of the air stream through the flow channel is measured or in that a temperature measurement of a reference resistance takes place, or in that the rotational speed of an impeller operated by the flow in the flow channel is measured. In this case, the control device would need to have an air inlet, which is in fluid communication with the flow channel.

Further details and features of embodiments of the present disclosure are described below with reference to the figures of preferred exemplary embodiments described in greater detail. These are only intended to illustrate the various embodiments, and in no way to limit them.

BRIEF DESCRIPTION OF THE DRAWINGS

FIG. 2 shows exemplary graphs for flow rate and aerosol production in the course of time in the case of inhalation controlled according to the method according to the invention.

DETAILED DESCRIPTION OF ILLUSTRATIVE EMBODIMENTS

Figure 1:
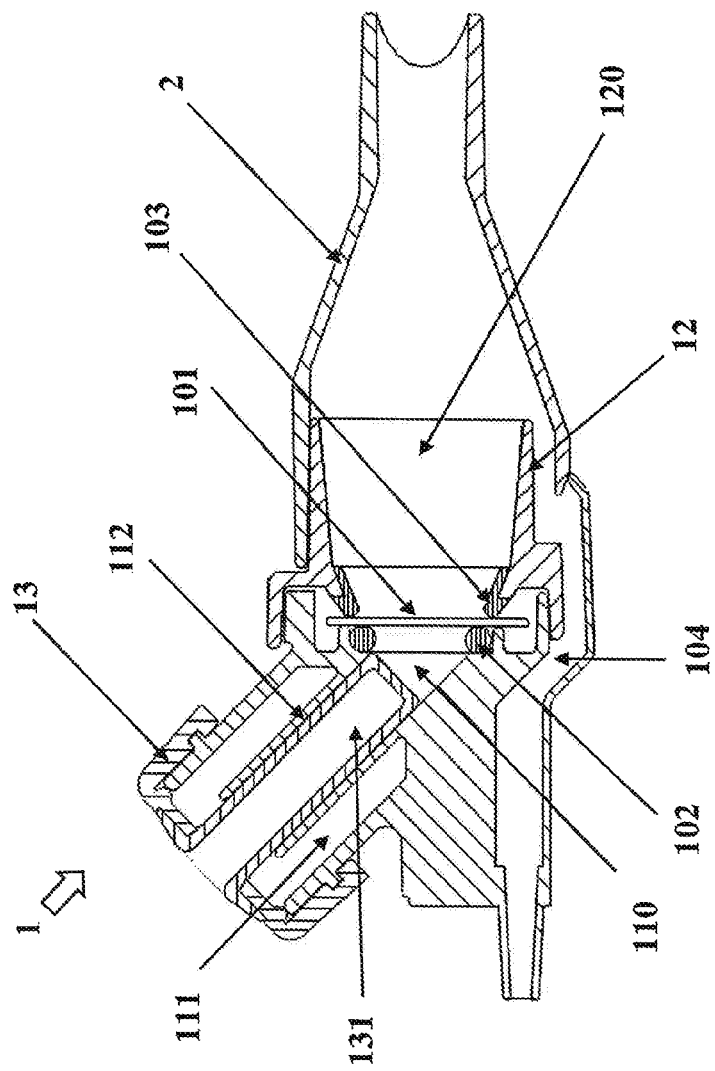
FIG. 1 shows a longitudinal section through the nebulizer unit, with mounted mouthpiece, of a preferred embodiment of the nebulizer according to the invention with flow channel.

FIG. 1 shows a longitudinal section through the nebulizer unit 1 with mounted mouthpiece of an embodiment of a nebulizer with flow channel according to embodiments of the present disclosure. The centrepiece of the nebulizer unit 1 is formed by the aerosol generator 101, which is mechanically retained by the sealing ring 102 and retaining structure 103. At the input end of the aerosol generator 101, the medication reservoir 11, which can be firmly sealed by a cap 13, can be seen, into which the liquid medication is filled. At the outlet end of the aerosol generator 101, there lies the aerosol chamber 120, an essentially cylindrical volume, in which the medication mist collects after atomization, before it is transported away through the mouthpiece 2 with the air stream generated by the user. The mouthpiece 2, for easier cleaning, is designed so as to be removable and in operation is plugged on a connecting piece 12, which is present on the nebulizer unit 1.

On the underside of the nebulizer unit, the flow channel 104 can be seen, which opens with its front end in the aerosol chamber 102, located in the outlet end of the aerosol generator 101, and with its second end is guided rearward, where it ends in a truncated conical nozzle, which can be connected to the control unit.

The opening of the flow channel 104 forms the reference point of the pressure measurement. It lies within that portion of the aerosol chamber 120 that is located in the mouthpiece 2, which has the decisive advantage that the measurable total pressure change is higher than that at a measurement point further in the direction of the aerosol generator 101. On one hand the respiratory cycle of the user can thus be more accurately monitored, on the other hand the pressure that is picked up there is also hardly influenced by shocks or general movements of the nebulizer, which advantageously further increases the accuracy.

FIG. 2 shows two graphs as an example of a time profile of flow rate $\dot{V}$ for two inhalation operations (top graph) as well as three different aerosol production rates $\dot{m}_1$, $\dot{m}_2$, $\dot{m}_3$, which are controlled according to embodiments of the present disclosure (lower graph).

As can be seen, with a first actuation process, dotted curve $\dot{m}_1$, the full aerosol production is triggered as soon as a threshold value $\dot{V}_1$ of the flow is exceeded, and stopped when it falls below a second threshold value $\dot{V}_2$.

The second aerosol production according to embodiments of the present disclosure, presented as a continuous line $\dot{m}_2$, provides, before the first threshold value $\dot{V}_1$ is reached, an activation with reduced production rate, which then, towards a threshold value $\dot{V}_3$, is increased to a maximum value, before, on falling below this threshold value $\dot{V}_3$, a reduction of the aerosol production starts, and this is eventually completely deactivated when the threshold value $\dot{V}_2$ is reached and fallen below.

As third, preferred mode of actuation, which is perhaps simplest to realize, dotted curve $\dot{m}_3$, embodiments of the present disclosure provide provides, after triggering on reaching the flow threshold value $\dot{V}_1$ to make the deactivation dependent on the expiry of a time span T.

LIST OF REFERENCE CHARACTERS

1 Nebulizer unit
11 Medication reservoir
12 Connecting piece for mouthpiece 2
13 Cap
101 Aerosol generator
102 Sealing ring
103 Retaining structure
104 Flow channel for connection to control unit
2 Mouthpiece
21 Aerosol chamber
$\dot{V}$ Flow rate
$\dot{V}_1$ First threshold value of the flow rate
$\dot{V}_2$ Second threshold value of the flow rate
$\dot{V}_3$ Third threshold value of the flow rate
$\dot{m}_1$ First aerosol production rate
$\dot{m}_2$ Second aerosol production rate
$\dot{m}_3$ Third aerosol production rate
T Time span Although the embodiments of the present disclosure have been described with reference to preferred embodiments, workers skilled in the art will recognize that changes may be made in form and detail without departing from the spirit and scope of the present disclosure.

The invention claimed is:

1. A nebulizer for carrying out an inhalation procedure comprising:
- a medication reservoir;
- a nebulizer unit including an aerosol generator configured to atomize a liquid medication supplied from the medication reservoir, and a connection piece;
- a mouthpiece attached to the connection piece of the nebulizer unit;
- an aerosol chamber formed by the nebulizer unit and the mouthpiece, the aerosol chamber being limited circumferentially by the connection piece and the mouthpiece and frontally by the aerosol generator;
- an air channel extending below the aerosol generator and having first and second ends, the first end connected to the aerosol chamber, and the second end extending rearwardly and including a protruding cone-shaped stub; and
- a control unit connected to the cone-shaped stub of the air channel and configured to monitor a pressure in, or a flow rate through the aerosol chamber using a pressure and/or flow rate sensor, wherein:
- air drawn from the outside into the aerosol chamber through an inhalation by a user enclosing the mouthpiece mixes with an aerosolization of the liquid medication generated by the aerosol generator to form a mixture that is transported through the mouthpiece and into the respiratory tracts and, if applicable, the lungs of the user; and
- the aerosolization unit is activated upon the detection of an activation criterion by the control unit, and deactivated upon detection of a stopping criterion by the control unit.

2. The nebulizer of claim 1, wherein the activation criterion includes the pressure or the flow rate exceeding a threshold value.

3. The nebulizer of claim 2, wherein, from a degree of fulfilment of the activation criterion, a weighted average value is calculated using the control unit, and the aerosol generator is activated when the weighted average value exceeds a threshold value.

4. The nebulizer of claim 1, wherein a rate of atomization of the liquid medication by the aerosol generator is controlled depending on a difference between the pressure and/or the flow rate and a threshold value for the pressure and/or the flow rate.

5. The nebulizer of claim 1, wherein the control unit is configured to calculate a total flow rate including integrating the measured flow rate over time.

6. The nebulizer of claim 1, wherein the control unit is configured to calculate a target attainment probability during each breath of a user.

7. The nebulizer of claim 1, wherein the stopping criterion includes one or more of the group consisting of:
an expiration of a time span;
the pressure exceeding a threshold pressure;
the flow rate falling below a threshold flow rate;
the flow rate reaching a preset total flow rate; and
a target attainment probability for a breath of the user calculated using the control unit that falls below a precalculated target attainment probability.

8. The nebulizer of claim 7, wherein, from a degree of fulfilment of the at least one stopping criterion, a weighted average value is calculated using the control unit, and the aerosol generator is deactivated as soon as the weighted average value exceeds a threshold value.

9. The nebulizer of claim 8, wherein weighting factors used in calculating the weighted average value are adapted during the course of an inhalation.

10. The nebulizer of claim 9, wherein, stop criteria in the form of a time span from a start of an inhalation are more strongly weighted at a beginning of an inhalation, and this weighting is changed over the course of an inhalation in favor of user-modified stop criteria selected from the group consisting of a total flow rate or falling below a target attainment probability.

11. The nebulizer of claim 1, wherein the pressure and/or flow rate sensor is configured to measure at least one of:
a dynamic pressure in the mouthpiece or an air channel leading to the mouthpiece;
a temperature of a reference resistor exposed to an air flow; and
a rotational speed of an impeller driven by an air flow.

12. The nebulizer of claim 1, wherein the at least one stop criterion includes a threshold value of a total flow rate that is adapted during the course of inhalation to total flow rate values corresponding to actual respiration volumes of the user.

13. A method for performing an inhalation using a nebulizer, the nebulizer including:
a medication reservoir;
a nebulizer unit including an aerosol generator and a connection piece;
a mouthpiece attached to the connection piece of the nebulizer unit;
an aerosol chamber formed by the nebulizer unit and the mouthpiece, the aerosol chamber being limited circumferentially by the connection piece and the mouthpiece and frontally by the aerosol generator;
an air channel extending below the aerosol generator and having first and second ends, the first end connected to the aerosol chamber, and the second end extending rearwardly and including a protruding cone-shaped stub; and
a control unit connected to the cone-shaped stub of the air channel and including a pressure and/or flow rate sensor,
the method comprising:
receiving the mouthpiece within the mouth of the user;
performing an inhalation by the user;
activating the aerosol generator and atomizing a liquid medication supplied from the medication reservoir upon detection of an activation criterion using the control unit;
mixing air drawn from the outside and the atomized liquid medication in the aerosol chamber;
transporting the mixed air and atomized liquid medication through the mouthpiece and into the respiratory tracts and, if applicable, the lungs of the user; and
deactivating the aerosol generator upon detection of a stopping criterion using the control unit.

14. The method of claim 13, wherein the activation criterion includes the pressure or the flow rate exceeding a threshold value.

15. The method of claim 14, further comprising calculating a weighted average value from a degree of fulfilment of the activation criterion using the control unit, wherein the aerosol generator is activated when the weighted average value exceeds a threshold value.

16. The method of claim 13, further comprising controlling a rate of atomization of the liquid medication by the aerosol generator depending on a difference between the pressure and/or the flow rate and a threshold value for the pressure and/or the flow rate.

17. The method of claim 13, further comprising calculating a total flow rate including integrating the measured flow rate over time using the control unit.

18. The method of claim 13, further comprising calculating a target attainment probability during each breath of a user using the control unit.

19. The method of claim 13, wherein the stopping criterion includes one or more of the group consisting of:
an expiration of a time span;
the pressure exceeding a threshold pressure;
the flow rate falling below a threshold flow rate;
the flow rate reaching a preset total flow rate; and
a target attainment probability for a breath of the user calculated using the control unit that falls below a precalculated target attainment probability.

20. The method of claim 19, further comprising calculating a weighted average value from a degree of fulfilment of the stopping criterion using the control unit, wherein the aerosol generator is deactivated as soon as the weighted average value exceeds a threshold value.

21. The method of claim 20, wherein weighting factors used in calculating the weighted average value are adapted during the course of an inhalation.

22. The method of claim 21, wherein, stop criteria in the form of a time span from a start of an inhalation are more strongly weighted at a beginning of an inhalation, and this weighting is changed over the course of an inhalation in favor of user-modified stop criteria selected from the group consisting of a total flow rate or falling below a target attainment probability.

23. The method of claim 13, wherein the pressure and/or flow rate sensor is configured to measure at least one of:
a dynamic pressure in the mouthpiece or an air channel leading to the mouthpiece;
a temperature of a reference resistor exposed to an air flow; and
a rotational speed of an impeller driven by an air flow.

24. The method of claim 13, wherein the stop criterion includes a threshold value of a total flow rate that is adapted during the course of inhalation to total flow rate values corresponding to actual respiration volumes of the user.

* * * * *